(12) United States Patent
Makarskyy et al.

(10) Patent No.: US 10,984,904 B1
(45) Date of Patent: Apr. 20, 2021

(54) COMPUTER SYSTEM FOR CONSTRUCTING GRAPHICAL USER INTERFACE FEATURES

(71) Applicant: Allscripts Software, LLC, Raleigh, NC (US)

(72) Inventors: Stanislav Makarskyy, Arlington Heights, IL (US); Mark Plunkett, Libertyville, IL (US)

(73) Assignee: Allscripts Software, LLC, Raleigh, NC (US)

( * ) Notice: Subject to any disclaimer, the term of this patent is extended or adjusted under 35 U.S.C. 154(b) by 181 days.

(21) Appl. No.: 15/935,845

(22) Filed: Mar. 26, 2018

(51) Int. Cl.
*G06F 17/00* (2019.01)
*G06F 3/00* (2006.01)
*G16H 30/20* (2018.01)
*G06F 9/451* (2018.01)
*G06F 3/0481* (2013.01)
*G06F 16/958* (2019.01)
*G06F 40/14* (2020.01)
*G06F 40/154* (2020.01)
*H04L 29/06* (2006.01)

(52) U.S. Cl.
CPC .......... *G16H 30/20* (2018.01); *G06F 3/0481* (2013.01); *G06F 9/451* (2018.02); *G06F 16/986* (2019.01); *G06F 40/14* (2020.01); *G06F 40/154* (2020.01); *H04L 67/42* (2013.01)

(58) Field of Classification Search
CPC .......... G06F 9/451; G06F 40/14; G16H 30/20
USPC ........................................ 715/746, 200, 234
See application file for complete search history.

(56) References Cited

U.S. PATENT DOCUMENTS

| | | | |
|---|---|---|---|
| 9,208,284 B1* | 12/2015 | Douglass | H04L 63/08 |
| 2013/0325490 A1* | 12/2013 | Abrahams | G06Q 50/22 705/2 |
| 2014/0058750 A1* | 2/2014 | Fotsch | G16H 10/60 705/3 |
| 2016/0098520 A1* | 4/2016 | Lulias | G16H 10/60 705/3 |
| 2019/0304582 A1* | 10/2019 | Blumenthal | G06F 9/451 |

* cited by examiner

*Primary Examiner* — Manglesh M Patel
(74) *Attorney, Agent, or Firm* — Medley, Behrens & Lewis, LLC

(57) ABSTRACT

A client computing device transmits a resource that conforms to a healthcare interoperability standard to a server computing device that executes a GUI generator component, and the GUI generator component generates GUI markup based upon the resource. The GUI generator component returns the GUI markup to the client computing device, which presents the GUI features on the a display based upon the GUI markup.

20 Claims, 5 Drawing Sheets

COMPUTER SYSTEM FOR CONSTRUCTING GRAPHICAL USER INTERFACE FEATURES

BACKGROUND

In healthcare information technology (IT), "interoperability" refers to the ability of different healthcare IT systems and software applications to communicate, exchange data, and use information that has been exchanged. In other words, when a healthcare software application exhibits interoperability, the healthcare software is able to work together within and across organizational boundaries with other healthcare software applications in order to advance the effective delivery of healthcare for individuals and communities. Various standards have been developed to support healthcare interoperability. Exemplary healthcare IT standards include the clinical document architecture (CDA) and the continuity of care record (CCR). Health Level-7 International (HL7) and the American Society for Testing and Materials (ASTM International) are the standards organizations that were respectively behind these aforementioned health IT standards. HL7 has subsequently set forth other standards, and relatively recently has set forth fast healthcare interoperability resources (FHIR) as a standard that describes data formats, elements (referred to as "resources"), as well as an application programming interface (API) for exchanging electronic health records. FHIR is relatively easy to implement for healthcare organizations, as such standard uses a modern web-based suite of API technology, including the Hypertext Transfer Protocol (HTTP)-based Representational State Transfer (REST)-ful protocol, Hypertext Markup Language (HTML) and Cascading Style Sheets (CSS) for user interface integration, a choice of Javascript Object Notation (JSON) or eXtensible Markup Language (XML) for data representation, and Atom (a web standard) for results.

Substitutable Medical Applications Reusable Technologies (SMART) health IT is an open standards-based technology platform that enables developers to create applications that seamlessly and securely run across a healthcare system. For example, using an electronic health record application (EHR) or data warehouse that supports the SMART standard, patients, doctors, and healthcare practitioners can draw on a library of SMART applications to improve clinical care, research, and public health. As FHIR has continued to gain support from the healthcare community, SMART has become a standard that works in conjunction with, and on top of, FHIR. Therefore, SMART focuses on formalizing the process for interacting with FHIR interfaces, outlining how applications will be launched from an EHR, and standardizing the security protocols used by third parties to exchange data with EHRs of healthcare organizations. Informally, then, FHIR defines the structure of where data should be retained and how the data should "look". An EHR is responsible for filling that structure with actual patient data. SMART defines how (possibly third party) applications launch from within an EHR, as well as to determine which EHR user is interacting with the application and to further determine an identity of a patient whose data is being accessed. SMART, however, in certain architectures, can impose restrictions that are cumbersome. In a nonlimiting example, a company may develop several EHRs. For instance, the company may develop an ambulatory EHR and an inpatient EHR. These two EHRs are designed to perform different functions in view of the different practices associated with hospital and ambulatory care, respectively. To decrease development and maintenance time, however, the organization that develops the two EHRs may develop applications that can be integrated with both EHRs. In another example, the organization that develops the two EHRs may choose to integrate one or more third party applications with the EHRs. For instance, to reduce development and maintenance time, a graphical user interface (GUI) generator component can be configured to generate GUI features for both the ambulatory EHR and the inpatient EHR. an application for generating certain graphical user interface (GUI) elements may be well-suited for use in both the ambulatory and inpatient EHR. Because the GUI generator application is designed to work with both types of EHRs (and therefore interoperability is desired), the EHRs and the GUI generator application can be designed to communicate with one another using protocols described in SMART.

In this scenario, however, conforming to SMART may impose limitations on what security frameworks/protocols can be used to authenticate a user, as well as sub-optimal performance. Specifically, following the procedures set forth by SMART, for an EHR to request generation of GUI features from the GUI generator application, the EHR emits a HTTP GET request to the SMART application endpoint (i.e., the GUI generator component). The HTTP GET request includes data that is indicative of the context of the EHR at the time of the HTTP GET request (e.g., an identity of a patient whose data is being presented to a clinician, an identity of a clinician, etc.). The HTTP GET request also includes metadata that points to the FHIR service layer of the EHR and optionally points to a security subsystem that is to handle authentication. The GUI generator component then calls the (exposed) FHIR service layer of the EHR to retrieve resources needed to generate the requested GUI features, constructs the GUI features based upon the resources, and causes the GUI features to be presented at a client device that initially requested the GUI features. When user input is received at the client computing device with respect to an interactive element at the GUI, the client computing device transmits an event message to the GUI generator component. The GUI generator component, in response to receiving this message, generates an another call to the FHIR service layer of the EHR, such that the EHR can provide the GUI generator component with any resources necessary to update the GUI features.

There are several disadvantages with respect to this approach. First, the EHR must expose its FHIR API layer to allow the GUI generator application to request resources, which is a security risk. Additionally, because of inherent limitations in HTTP GET requests, certain types of security tokens cannot be used to authenticate to the GUI generator component. Moreover, as described above, each time the client computing device generates an event message based upon user interface with one of the GUI features generated by the GUI generator component, the GUI generator component must transmit a call to the FHIR API layer of the EHR. These additional communications result in sub-optimal communications and security risks.

SUMMARY

The following is a brief summary of subject matter that is described in greater detail herein. This summary is not intended to be limiting as to the scope of the claims.

Described herein are various technologies for generating GUI features for an EHR, wherein the GUI features are to be presented on a display of a client computing device. The technologies described herein are improvements over conventional technologies for generating GUI features for EHRs, as the technologies described herein support the use of security tokens that are not natively supported in the conventional technologies. In addition, the technologies described herein do not require exposure of an FHIR API layer of the EHR, thereby improving security relative to conventional technologies.

In operation, a client computing device executing a client EHR receives input from a user to initiate (launch) an application from a server EHR, wherein, in an example, the application is a GUI generator component that is configured to generate GUI features for presentment on a display of the client computing device, and further wherein an EHR comprises the server EHR and client EHRs executing on client computing devices (including the client EHR referenced above). The client EHR, responsive to receiving the input, causes the client computing device to transmit a request to a server computing device executing the server EHR, whereupon the server EHR is provided with such request. Responsive to receiving such request, the server EHR receives or constructs resources for generating the GUI features, wherein the resources conform to a healthcare interoperability standard, such as FHIR. For example, the server EHR can receive resources from a web service and/or can generate resources (if generation of the resources is supported natively by the server-side EHR). Additionally, and optionally, the server EHR can construct a security token or receive a security token from a security subsystem, wherein the security token can be a Security Assertion Markup Language (SAML) token. Responsive to obtaining the aforementioned resources and the security token, the server EHR can optionally compress the resources and the security token and cause the server computing device to transmit the resources and the security token to the client computing device. In an example, the server EHR can construct a self-posting form, and can transmit the self-posting form and the resources and security token to the client computing device.

In response to receiving the resources and the security token, the client computing device provides such data to the client EHR, which may be executed by a web browser. The client EHR constructs an HTTP POST request and populates the request with the resources and the security token. Instructions for generating the HTTP POST request, including content that is to be included in the request and destination of the request, are included in the self-posting form and/or are transmitted with the self-posting form. Because an HTTP POST request is used instead of an HTTP GET request, the payload is not limited to 2 kilobytes. The client EHR thereafter causes the client computing device to transmit the HTTP POST request to a second server computing device that executes the GUI component.

The second server computing device receives the HTTP POST request, whereupon content of the HTTP POST request (the resources and the security token) is provided to the GUI generator application. The second server computing device authenticates the client EHR based upon the security token, and and constructs computer-executable code that, when executed by the browser, results in generation of the requested GUI features in the browser that executes the client EHR. For example, the computer-executable code can include HTML, instructions written in scripting language (e.g., JavaScript), CSS, etc. Hence, the browser executing on the client computing device renders the requested GUI features.

The client computing device can present the rendered GUI features on the display of the client computing device, and subsequently the client EHR can receive input from the user with respect to one of the GUI features, such as entry of data into a text entry field, a mouse click, keystrokes, etc. As indicated previously, the GUI features may be presented in a self-posting form; accordingly, when the user selects an "OK" button or the like, the self-posting form captures the user data set forth in the self-posting form. Code written in scripting language (e.g., JavaScript) detects this user data, and transfers to user data outside of the self-posting form (to the client EHR executing in the browser), and the client EHR subsequently causes the client computing device to transfer an event message to the server computing device that executes the server EHR. The server EHR receives the event message, and performs an appropriate action in response to the event message (e.g., performs a search over a database, etc.). Accordingly, unlike conventional technologies, the event message need not be passed from the client computing device to the second server computing device that executes the GUI generator component (where the GUI generator component would then transmit a call back to the server EHR via the exposed FHIR service API).

In summary, using the technologies described above, the server EHR need not expose the FHIR API of the server EHR to allow for calls by an external application. Further, since the client computing device transmits data to the second server computing device that executes the GUI component by way of an HTTP POST request, string limitations associated with the conventional technologies (which use HTTP GET requests) do not exist, and thus large amounts of data can be passed to the GUI generator component, including the required input/context data and larger security tokens. Still further, the client-side event model described above is an efficient and secure way of passing data between applications, as it replaces an additional FHIR API call that would have to be made to the service EHR by way of an exposed API. Moreover, the GUI generator application can be independently hosted and versioned, which enables rapid feature delivery for EHRs with longer release cycles, especially on-premises EHRs.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
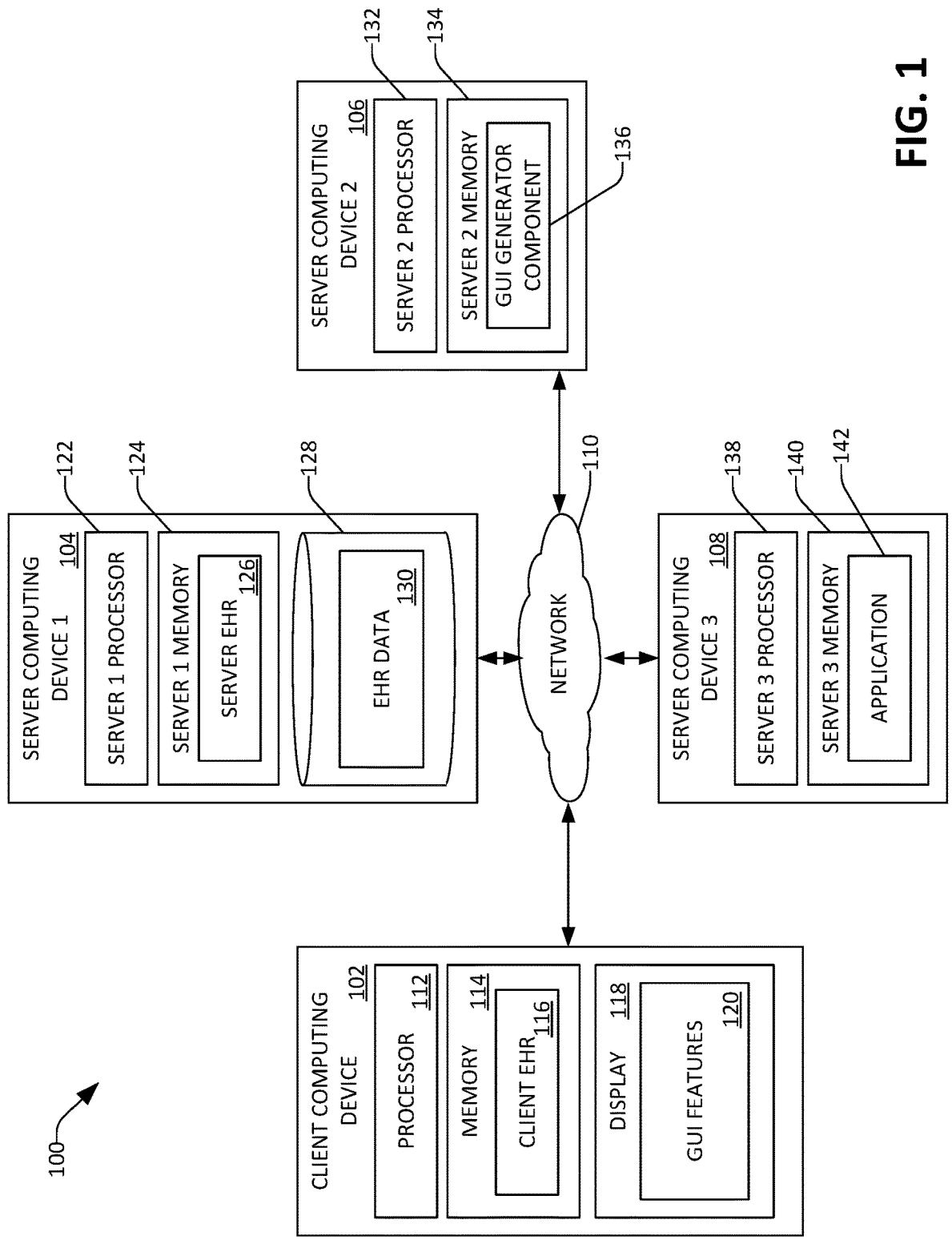
FIG. 1 is a functional block diagram of an exemplary system that facilitates construction of GUI features for an EHR.

Various technologies pertaining to construction of GUI features for presentment on a display of a client computing device are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

The various technologies described herein relate to the healthcare IT environment, wherein the technologies relate more specifically to provision of resources to a computer-executable application that executes in conjunction with an EHR and is interoperable with the EHR (and other EHRs). An EHR is a distributed application that includes a server EHR that provides server-side functionality and a client EHR that provides client-side functionality. The client EHR is configured to display data (e.g., patient data) to a clinician who is operating a client computing device, as well as receive input from the clinician with respect to patients. The server EHR is configured to perform searches for data related to patients, maintain electronic health records about patients, order lab tests for patients, prescribe medication for patients, and so forth. Further, as noted above, healthcare systems can have interoperability with one another—and therefore, EHRs can be integrated with several different applications. In a nonlimiting example, an EHR can be integrated with a prescription pricing application that is configured to search inventories of pharmacies for prescription medication and corresponding pricing. Accordingly, the EHR is configured to call such application, and the application returns prescription medication identities and corresponding price information back to the EHR.

Further, as noted previously, an organization may develop several different EHRs for provision to different types of healthcare organizations. In a nonlimiting example, an organization can develop and maintain a first EHR for ambulatory organizations and can develop and maintain a second EHR for inpatient organizations. To reduce development and maintenance requirements, both the first and second EHR can be integrated with a GUI generator application that can generate GUI features for both the first and second EHR. The technologies described herein relate to providing these applications (that are interoperable with EHRs) with resources that conform to healthcare interoperability standards (such as HL7, FHIR, etc.) while enhancing performance and reducing security risk when compared to conventional approaches.

With reference now to FIG. 1, a functional block diagram of an exemplary system 100 is illustrated. The system 100 comprises a client computing device 102, a first server computing device 104, a second server computing device 106, and (optionally) a third server computing device 108. The client computing device 102 and the server computing devices 104, 106, and 108 are in communication with one another by way of a network 110. While the system 100 illustrates existence of a single network 110, it is to be understood that multiple networks may be employed to allow for the client computing device 102, the server computing device 104, the second server computing device 106, and the third server computing device 108 to communicate with one another.

The client computing device 102 can be any suitable type of client computing device, including, but not limited to, a desktop computing device, a tablet computing device, a laptop computing device, a mobile telephone, a wearable computing device (augmented reality headgear, a watch, etc.), or the like. The client computing device 102 comprises a processor 112 and memory 114 that has a client EHR 116 loaded therein. In an example, the client EHR 116 can be a browser-based EHR, such that the client computing device 102 executes a web browser, and the EHR 116 executes in the web browser. The client computing device 102 also includes a display 118, which is configured to present GUI features 120 of the client EHR 116 thereon. The GUI features 120 can be presented on the display 118 by the processor 112 when executing the client EHR 116. In other words, the client EHR 116, when executed by the processor 112, can cause the GUI features 120 to be shown on the display 118.

The first server computing device 104 includes a first server processor 122 and first server memory 124, wherein the first server memory 124 has a server EHR 126 loaded therein. The first server computing device 104 also includes a data store 128 that retains EHR data 130. This EHR data 130 can include clinical data (e.g., electronic health records about patients), amongst other data typically retained in a backend EHR database. Generally, the server EHR 126 is configured to receive messages from the client EHR 116 and respond to such messages. For instance, a clinician operating the client computing device 102 may submit a request for electronic health data about a patient by way of the client EHR 116, which causes the client computing device 102 to transmit a message to the server EHR 126. The server EHR 126, in response to receiving such request, conducts a search over the EHR data 130, locates data about the patient, and causes the first server computing device 104 to transmit such data to the client computing device 102, whereupon the client EHR 116 can cause the data to be shown on the display 118.

The second server computing device 106 includes a second server processor 132 and second server memory 134, wherein the second server memory 134 had loaded therein a GUI generator component 136. The GUI generator component 136 may be a third-party application, such that an organization that developed the GUI generator component 136 is different from the organization that developed the client EHR 116 and the server EHR 126. In another example, the GUI generator component 136 may be developed by the same organization that developed the client EHR 116 and the server EHR 126, but the GUI generator component 136 is configured to be interoperable with at least one other EHR. Allowing for interoperability in this manner reduces development time and cost and further reduces maintenance time and cost.

The third server computing device 108 includes a third server processor 138 and third server memory 140, wherein the third server memory 140 has loaded therein a computer-executable application 142 that generates data that is to be represented in the GUI features 120 on the display 118 of the client computing device 102. In an example, the application 142 can be configured to retrieve price information for prescription medications that may be prescribed to a patient who is being provided care by a clinician who is operating the client computing device 102. As indicated previously, however, the GUI generator component 136 is tasked with constructing the GUI features 120. Accordingly, the client computing device 102 and the server computing devices 104-108 are to communicate with one another securely and efficiently, while nevertheless providing the GUI generator component 136 with the requisite resources for constructing the GUI features 120 for presentment on the display 118 of the client computing device 102.

While the server EHR 126, the GUI generator component 136, and the application 142 are illustrated as executing on separate server computing devices, it is to be understood that the server EHR 126, the GUI generator component 136, and/or the application 142 may execute on fewer server computing devices. For instance, a server computing device may execute several virtual machines, and the server EHR 126, the GUI generator component 136, and the application 142 may execute in the virtual machines on the server computing device. Moreover, while the system 100 is illustrated as including the third server computing device 108, such device 108 may be optional. For example, the server EHR 126 may be configured to perform actions described as being performed by the application 142. Other arrangements are also contemplated A brief description of the operation of the system 100 is now set forth. The client EHR 116 receives input from a user that indicates that the computer-executable application 142 is to be launched and/or data is to be retrieved from the application 142. Responsive to receiving this input, the client EHR 116 causes the client computing device 102 to transmit a message to the first server computing device 104, whereupon the server EHR 126 is provided with the message. In the exemplary system 100, the server EHR 126 then causes the first server computing device 104 to transmit a request to the third server computing device 108 for resources that conform to a healthcare interoperability standard (e.g., FHIR). In the example described above, these resources can represent price data for prescription medication that is available at at least one pharmacy. The application 142 generates the requested resources, and causes the third server computing device 108 to transmit a message back to the first server computing device 104, wherein the message includes the resources requested by the server EHR 126.

The first server computing device 104 receives the resources from the third server computing device 108, whereupon the resources are provided to the server EHR 126. The server EHR 126 optionally, generates a security token or retrieves a security token from a security subsystem (not shown). The server EHR 126 then causes the server computing device 104 to transmit the resources and the security token to the client computing device 102. In a nonlimiting example, the server EHR 126 can construct a self-posting form, which is an HTML form that, when executed by a browser, causes data in the form to be posted back to the form, and thus to the browser. Thus, the self-posting form can include instructions that cause the browser to emit an HTTP POST message to a Uniform Resource Locator (URL), wherein the URL is specified in the instructions. Moreover, the self-posting form can include the requested resources and the security token.

The client computing device 102 receives the self-posting form, whereupon the web browser (which executes the client 116) is provided with the self-posting form. The web browser loads the self-posting form, and based upon the instructions therein, causes the client computing device 102 to transmit an HTTP POST request to the second server computing device 106. Such HTTP POST request is not associated with payload size limitations of HTTP GET requests, and therefore the HTTP POST request can include the resources received from the server EHR 126 and the security token received from the server EHR 126. Due to the lack of size limitations, the security token can be a relatively large token, such as an SAML token. The GUI generator component 136 receives the resources and the security token, and authenticates the client EHR 116 based upon the security token. The GUI generator component 136, responsive to authenticating the client EHR 116 and receiving the resources, generates a GUI markup that, when executed by the web browser, causes the client computing device 102 to present the GUI features 120 on the display 118 of the client computing device 102. For example, the GUI markup can include HTML, instructions written in a scripting language (e.g., JavaScript), CSS, and/or other browser-executable instructions. The GUI generator component 136 can then cause the GUI markup to be transmitted by the second server computing device 106 back to the client computing device 102. The web browser executing the client EHR 116 receives the GUI markup, executes instructions in the markup, and causes the GUI features 120 to be shown on the display 118 (e.g., in the space previously allocated to the self-posting form) in an HTML form. Therefore, in the example described above, the GUI features 120 can include prescription medication price information.

The GUI features 120 can include interactive elements, such that the clinician operating the client computing device 102 can set forth input to one or more interactive elements. In an example, a clinician operating the client computing device 102 can set forth input requesting additional information about a prescription medication represented in the GUI features 120. As noted previously, the HTML form received from the GUI generator component 136 includes instructions (e.g., written in a scripting language) for detecting such input. Responsive to the input being detected, a scripting language event message is generated and passed to the client EHR 116. The client EHR 116 can receive the event message, optionally process the event message, and transmit data to the server EHR 126, whereupon the server EHR 126 can perform an appropriate action based upon the data (e.g., the server EHR 126 can make an outbound database call in response to receipt of the data).

As mentioned previously, there are several differences in the manner in which the computing devices of the system 100 communicate with one another when compared to conventional approaches set forth by SMART. Specifically, rather than the client EHR 116 providing the GUI generator component 136 with all the information that it needs to generate the GUI features 120 (the resources and security token), SMART requires that the client EHR 116 provides the GUI generator component 136 with metadata that includes cues to retrieve such information. SMART then requires that the GUI generator component 136 call back to the server EHR 126 to obtain the resources that it needs to generate the GUI features 120. This poses additional security challenges, as the server EHR 126 must expose its FHIR API to the GUI generator component 136. Further, the approach described herein allows for detected user input at the client with respect to the GUI features 120 to be transmitted directly to the server EHR 126, rather than routed to the server EHR 126 by way of the GUI generator component 136; hence, the approaches described herein require fewer communications when compared to conventional approaches.

Figure 2:
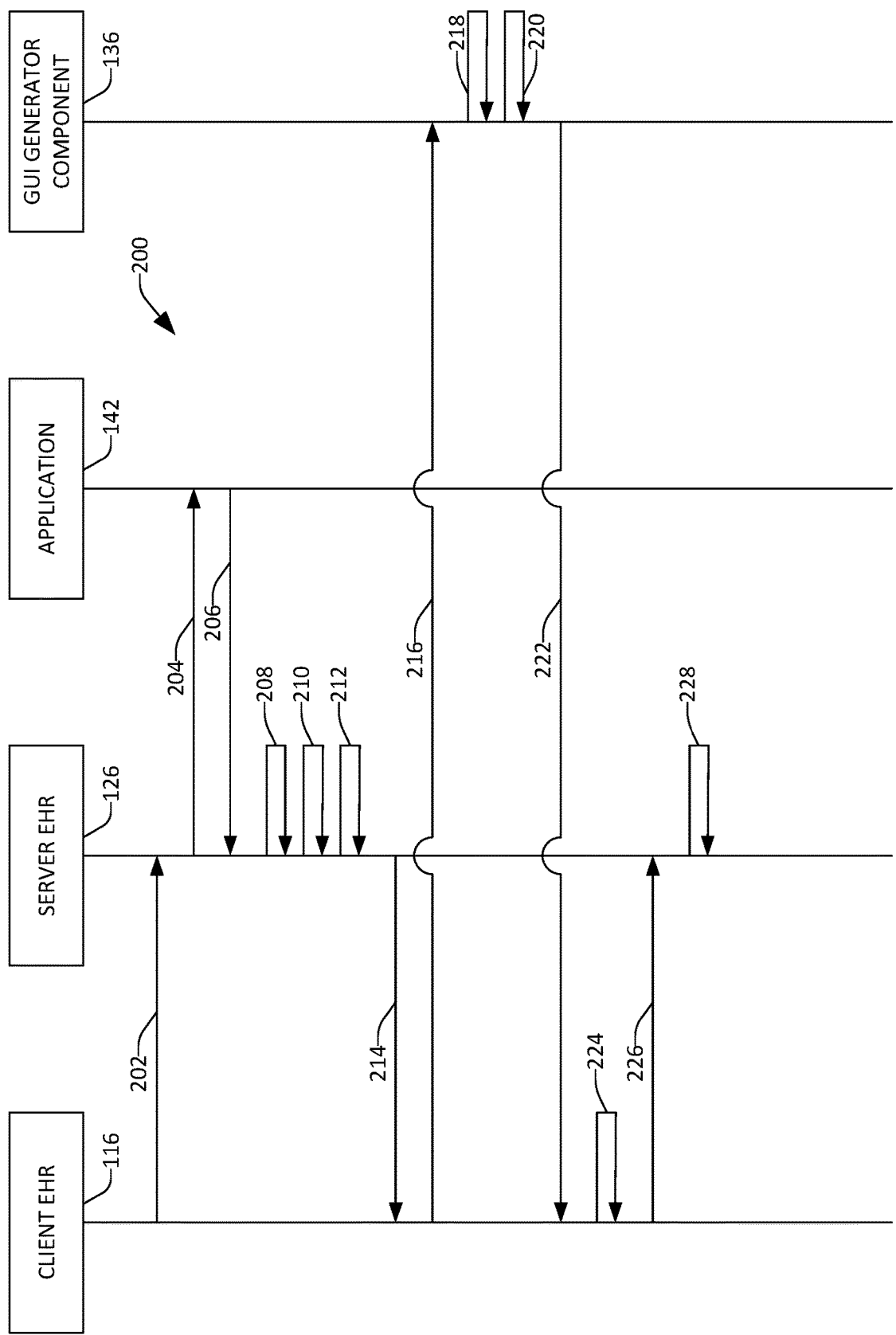
FIG. 2 is a communications diagram that illustrates communications between components of the system shown in FIG. 1.

Now referring to FIG. 2, an exemplary communications diagram 200 that illustrates communications transmitted amongst and between the client EHR 116, the server EHR 126, the computer-executable application 142, and the GUI generator component 136 is presented. Initially, the client EHR 116 receives an indication that a user of the client computing device 102 has requested data from the application 142 (wherein the application 142 may be integrated with the server EHR 126 or separate from the server EHR 126). At 202, the client EHR 116 transmits a message that is indicative of this request to the server EHR 126. Responsive to receiving the message, at 204, the server EHR 126 optionally transmits a request to the application 142 for resources (that conform to a healthcare interoperability standard) that are to be presented in the GUI features 120. At 206, the application 142 transmits a response to the request, wherein the response includes the requested resources (and optionally custom data generated by the application 142). Communications 204 and 206 are optional, as the server EHR 126 (as noted above) may include the functionality of the application 142, and may generate the resources and (optionally) the custom data itself.

At 208, responsive to receiving the request from the client EHR 116 at 202, the server EHR 126 optionally constructs a request that includes resources needed by the GUI generator component 136 to cause the requested GUI features 120 to be shown on the display 118 of the client computing device 102. In an alternative embodiment, the request is constructed by the application 142 and provided to the server EHR 126. The request includes the resources and/or custom data referenced above. At 210, responsive to receiving the request from the client EHR 116 at 202, the server EHR 126 generates a security token, such as an SAML token. In another exemplary embodiment, the server EHR 126 requests the security token from a security subsystem that is in communication with the server EHR 126 (instead of generating the security token). At 212, the server EHR 126 constructs a self-posting HTML form, wherein the self-posting HTML form is constructed to comprise the resources (and custom data) and the security token. Optionally, the server EHR 126 can compress the resources and/or security token prior to including the resources and/or security token in the self-posting HTML form. Still further, the self-posting HTML form comprises instructions that, when executed by the web browser that hosts the client EHR 116, causes the web browser to transmit a message directed to the GUI generator component 136.

At 214, the server EHR 126 transmits the self-posting HTML form to the client EHR 116. A developer of the client EHR 116 can specify where, in the GUI of the client EHR 116, the self-posting HTML form is to be allocated space in the GUI of the client EHR 116. Responsive to receiving the self-posting HTML form, the web browser executing the client EHR 116 loads the self-posting HTML form, which includes the instructions referenced above. The instructions, when interpreted by the browser, cause the web browser to construct an HTTP POST request, wherein the HTTP POST request comprises the (compressed) resources and security token. At 216, the client EHR transmits the HTTP POST request to the GUI generator component 136.

At 218, the GUI generator component 136 authenticates the client EHR 116 based upon the security token. At 220, the GUI generator component 136 constructs GUI markup, which includes, for example, HTML code, code written in a scripting language, CSS, and other suitable content that can be executed by the web browser that hosts the client EHR 116. The GUI generator component 136 constructs the GUI markup based upon the payload of the HTTP POST request (the resources). In the embodiment where the resources are compressed in the HTTP POST request, the GUI generator component 136 can decompress the compressed resources. At 222, the GUI generator component 136 transmits the GUI markup to the client EHR 116, whereupon the browser constructs an HTML form that includes the GUI features 120 based upon the GUI markup. Further, the HTML form is included in the space previously allocated to the self-posting HTML form.

As mentioned previously, the GUI features 120 can include interactive elements, such as text entry fields, radio buttons, pulldown menus, and so forth, such that the clinician operating the client computing device 102 can set forth input with respect to one or more of the GUI features 120 presented on the display 118. For example, the clinician can set forth text into a text entry field, the clinician can select a toggle (via mouse click or touch), can select a check box (via mouse click or touch), etc. At 224, the input is collected by the page shown on the display 118, and upon some user-triggered action (e.g., selection of a button), the instructions in the GUI markup (e.g., the HTML form) detect the user-triggered input and raise a client-side event message that is passed from the HTML form to the client EHR 116. At 226, the client EHR transmits data to the server EHR 126, wherein the data is based upon content of the client-side event message. At 228, the server EHR 126 processes the data received from the client EHR 116. For example, the server EHR 126 can perform a search over a database based upon the event message, may request additional resources from the application 142, etc.

As noted previously, there are various advantages to the approach shown in FIG. 2. For instance, there is no need for the server EHR 126 to expose an API that is to be called by an external application, wherein the API is configured to communicate resources that conform to a healthcare interoperability standard. Further, since URL string limitations are not applicable to HTTP POST requests, the client EHR 116 can transmit a large amount of data to the GUI generator component 136, including resources and context data, as well as relatively large security tokens. Still further, the client EHR 116 can transmit context data to the GUI generator component 136 directly, thereby potentially reducing calls to the server EHR 126 that would otherwise need to be made by the GUI generator component 136. Moreover, the passing of events, using code written in scripting language on the client computing device 102, is an efficient and secure way of passing data between the client EHR 116 and the server EHR 126, as it replaces an additional API call to the server EHR 126 that would have to be made otherwise (e.g., otherwise, the client EHR 116 must transmit a message to the GUI generator component 136, which in turn must call the server EHR 126). Finally, the GUI generator component 136 can be independently hosted and versioned, thereby enabling rapid feature delivery for EHRs having longer release cycles, especially on-premises EHRs.

Figure 3:
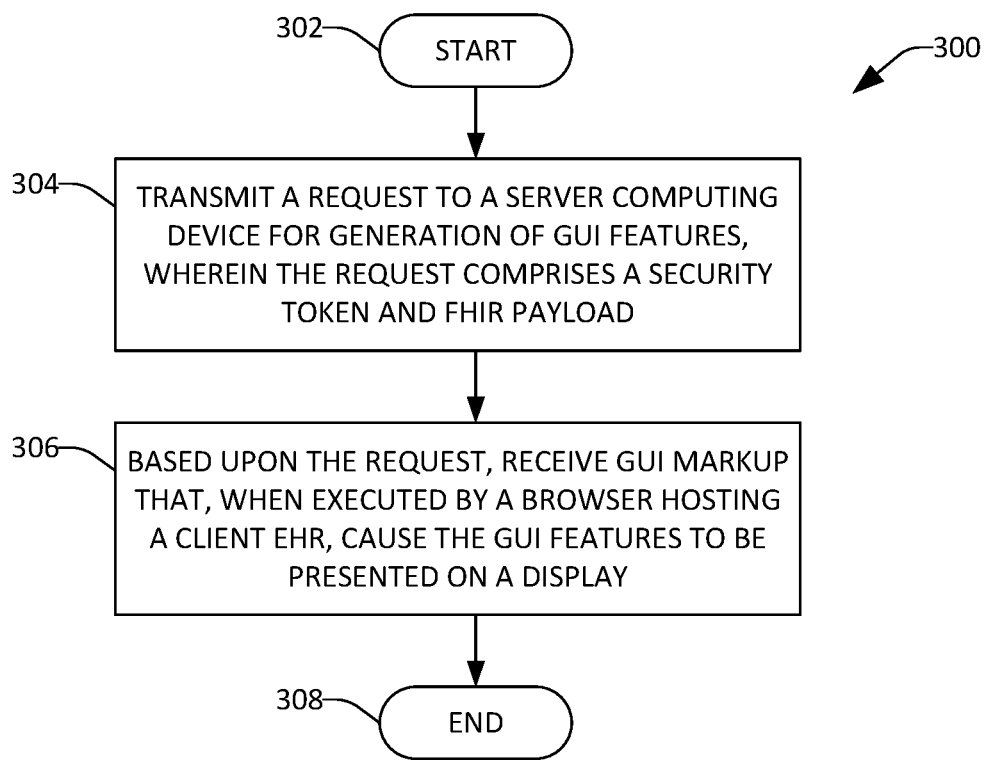
FIG. 3 is a flow diagram illustrating an exemplary methodology for presenting GUI features on a display of a client computing device.
Figure 4:
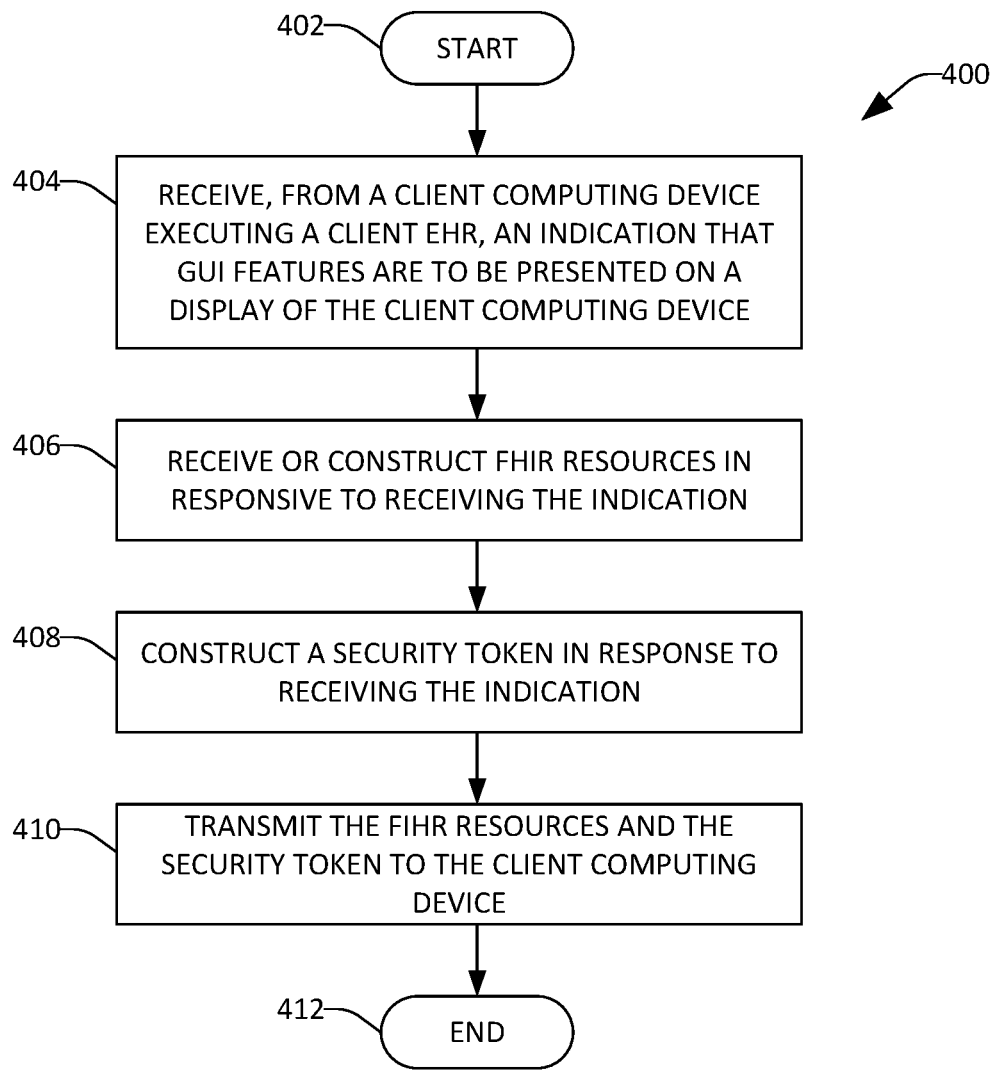
FIG. 4 is a flow diagram illustrating an exemplary methodology for providing a GUI generator component with resources that are usable to GUI features for presentment on a client computing device.

FIGS. 3 and 4 illustrate exemplary methodologies relating to presenting GUI features on a display of a client computing device. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring to FIG. 3, an exemplary methodology 300 that can be executed by the client computing device 102 is illustrated. The methodology 300 starts at 302, and at 304, a request (e.g., an HTTP POST request) is transmitted to a server computing device, wherein the server computing device executes the GUI generator component 136. The request comprises a security token and FHIR payload (FHIR resources that are to be used by the GUI generator component 136 to construct the GUI markup). At 306, based upon the request, computer-executable instructions are received, that, when executed by a browser that hosts a client EHR, cause the GUI features to be presented on a display of the client computing device. The methodology 300 completes at 308.

Now referring to FIG. 4, an exemplary methodology 400 that can be executed by the first server computing device 104 is illustrated. The methodology 400 starts at 402, and at 404, an indication is received from a client computing device executing a client EHR that GUI features are to be presented on a display of the client computing device. At 406, FHIR resources are received or constructed in response to receiving the indication at 404. For instance, when the FHIR resources are received, the server computing device 104 can request the FHIR resources from a web service. At 408, a security token is constructed (or received) in response to receiving the indication. At 408, the FHIR resources and the security token are transmitted to the client computing device, whereupon the client computing device can transmit the FHIR resources and the security token to the GUI generator component 136. The methodology 400 completes at 410.

Figure 5:
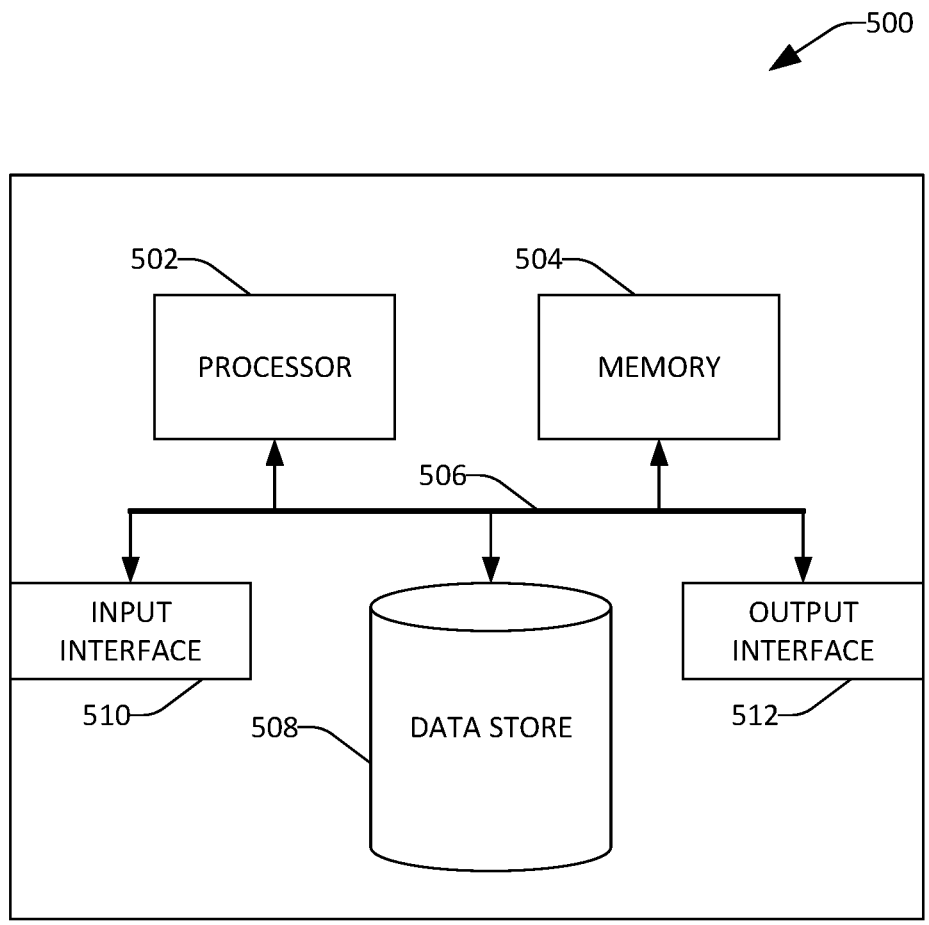
FIG. 5 is an exemplary computing system.

Referring now to FIG. 5, a high-level illustration of an exemplary computing device 500 that can be used in accordance with the systems and methodologies disclosed herein is illustrated. For instance, the computing device 500 may be used in a system that supports constructing GUI markup. By way of another example, the computing device 500 can be used in a system that presents GUI features on a display. The computing device 500 includes at least one processor 502 that executes instructions that are stored in a memory 504. The instructions may be, for instance, instructions for implementing functionality described as being carried out by one or more components discussed above or instructions for implementing one or more of the methods described above. The processor 502 may access the memory 504 by way of a system bus 506. In addition to storing executable instructions, the memory 504 may also store GUI features, patient data, etc.

The computing device 500 additionally includes a data store 508 that is accessible by the processor 502 by way of the system bus 506. The data store 508 may include executable instructions, patient data, etc. The computing device 500 also includes an input interface 510 that allows external devices to communicate with the computing device 500. For instance, the input interface 510 may be used to receive instructions from an external computer device, from a user, etc. The computing device 500 also includes an output interface 512 that interfaces the computing device 500 with one or more external devices. For example, the computing device 500 may display text, images, etc. by way of the output interface 512.

It is contemplated that the external devices that communicate with the computing device 500 via the input interface 510 and the output interface 512 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 500 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 500 may be a distributed system. Thus, for instance, several devices may be in communication by way of a network connection and may collectively perform tasks described as being performed by the computing device 500.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A client computing device, comprising:
    a processor; and
    memory storing a client electronic health record (EHR) application, wherein the client EHR application, when executed by the processor, causes the processor to perform acts comprising:
        transmitting, to a server EHR application executing on a server computing device, an indication that graphical user interface (GUI) features are to be constructed for the client EHR application, wherein the GUI features are to be displayed on a display of the client computing device, and further wherein the client computing device and the server computing device are in communication over a network connection, wherein the server EHR application constructs a self-posting form responsive to receiving the indication and transmits the self-posting form to the client EHR application, wherein the self-posting form comprises a resource output by the server EHR application, the resource conforming to a healthcare interoperability standard, wherein the resource comprises healthcare data of a patient, wherein the self-posting form is a Hypertext Markup Language (HTML) form that is configured to cause the client EHR application to transmit the resource to a GUI markup application executing on a second server computing device responsive to being loaded by the client EHR application, the GUI markup application is configured to generate GUI markups for multiple different EHR applications that each maintain respective patient health records, wherein the client computing device and the second server computing device are in communication over a second network connection;
        responsive to transmitting the indication to the server EHR application, receiving, from the server EHR application and over the network connection the self-posting form;
        responsive to receiving the self-posting form from the server EHR application, transmitting the resource to the GUI markup application, wherein the GUI markup application generates a GUI markup based upon the resource;
        subsequent to transmitting the resource to the GUI markup application, receiving, from the GUI markup application and over the second network connection, the GUI markup; and
        responsive to receiving the GUI markup, rendering the GUI features on the display of the client computing device based upon the GUI markup, wherein the GUI features include the resource.

2. The client computing device of claim 1, wherein a web browser hosts the client EHR application.

3. The client computing device of claim 1, wherein the healthcare interoperability standard is the Fast Healthcare Interoperability Resources (FHIR) standard.

4. The client computing device of claim 1, the acts further comprising:
    responsive to transmitting the indication to the server EHR application, receiving, from the server EHR application and over the network connection, a security token output by the server EHR application; and
    responsive to receiving the security token from the server EHR application, transmitting the security token to the second server computing device, wherein the second server computing device authenticates the client EHR application based upon the security token, and further wherein the GUI markup application transmits the GUI markup to the client computing device only after authentication of the client EHR application based upon the security token.

5. The client computing device of claim 1, wherein the resource is compressed when transmitted to the GUI markup application.

6. The client computing device of claim 1, wherein transmitting the resource to the GUI markup application comprises:
    generating a Hypertext Transfer Protocol (HTTP) POST request, wherein the HTTP POST request comprises the resource.

7. The client computing device of claim 6, the acts further comprising:
    responsive to transmitting the indication to the server EHR application, receiving, from the server EHR application and over the network connection, a security token output by the server EHR application; and
    responsive to receiving the security token from the server EHR application, transmitting the security token to the second server computing device as part of the HTTP POST request.

8. The client computing device of claim 6, wherein the self-posting form causes the client EHR to generate the HTTP POST request.

9. The client computing device of claim 1, wherein the self-posting form is assigned to a region on the display of the client computing device, and further wherein the GUI features are rendered in the region assigned to the self-posting form.

10. The client computing device of claim 9, wherein the GUI features, when rendered on the display of the client computing device, comprise an interactive element, the acts further comprising:
- receiving user input with respect to the interactive element;
- responsive to receiving the user input with respect to the interactive element, passing an event message to a web browser that hosts the client EHR application; and
- responsive to passing the event message to the web browser, transmitting data to the server computing device, whereupon the data is provided to the server EHR application, and wherein the server EHR application executes a search based upon the data and responsive to receiving the data, wherein the data is based upon the event message.

11. A method executed by a client computing device that is in network communication with a first server computing device and a second server computing device, wherein the client computing device executes a client electronic health record (EHR) application, the first server computing device executes a server EHR application, and the second server computing device executes a GUI markup application that is configured to construct GUI markups for multiple different EHR applications that each maintain respective patient health records, the method comprising:
- transmitting, to the server EHR application, an indication that a GUI markup is to be constructed for the client EHR application, wherein GUI features defined in the GUI markup are to be displayed on a display of the client computing device, wherein the server EHR application constructs a self-posting form responsive to receiving the indication and transmits the self-posting form to the client EHR application, wherein the self-posting form comprises a resource output by the server EHR application, the resource conforming to a healthcare interoperability standard, wherein the resource comprises healthcare data of a patient, wherein the self-posting form is a Hypertext Markup Language (HTML) form that is configured to cause the client computing device to transmit the resource to the second server computing device that executes the GUI markup application responsive to being loaded by the client EHR application;
- responsive to transmitting the indication to the server EHR application, receiving, from the server EHR application, the self-posting form;
- responsive to receiving the self-posting form from the server EHR application, transmitting the resource to the GUI markup application, wherein the GUI markup application generates the GUI markup based upon the resource received from the client EHR application;
- subsequent to transmitting the resource to the GUI markup application, receiving, from the GUI markup application, the GUI markup; and
- responsive to receiving the GUI markup, rendering the GUI features on the display of the client computing device based upon GUI markup, wherein the GUI features include the resource.

12. The method of claim 11, wherein the server EHR application constructs the resource responsive to receiving the indication from the client EHR application.

13. The method of claim 11, wherein the server EHR application retrieves the resource from an application executing on a third server computing device responsive to receiving the indication from the client EHR application.

14. The method of claim 11, wherein the healthcare interoperability standard is the Fast Healthcare Interoperability Resources (FHIR) standard.

15. The method of claim 11, wherein the client computing device is a mobile telephone.

16. The method of claim 11, wherein the GUI markup comprises hypertext markup language (HTML) code, code written in a scripting language, and code written in Cascading Style Sheets.

17. The method of claim 11, wherein transmitting the resource to the server EHR application comprises constructing a Hypertext Transfer Protocol (HTTP) POST request, wherein the resource is included in the HTTP POST request.

18. The method of claim 17, further comprising transmitting a security token to the second server computing device, wherein the security token is included in the HTTP POST request.

19. The method of claim 18, wherein the security token is a Security Assertion Markup Language (SAML) token.

20. A client computing device that comprises a computer-readable storage medium, wherein the computer-readable storage medium comprises a client electronic health record (EHR) application that, when executed by a processor, causes the processor to perform acts comprising:
- transmitting, to a server EHR application executing a server computing device, an indication that graphical user interface (GUI) features are to be constructed for the client EHR application, wherein the GUI features are to be displayed on a display of the client computing device, and further wherein the client computing device and the server computing device are in communication over a network connection, wherein the server EHR application constructs a self-posting form responsive to receiving the indication and transmits the self-posting form to the client EHR application, wherein the self-posting form comprises a resource output by the server EHR application, the resource conforming to a healthcare interoperability standard, wherein the resource comprises healthcare data of a patient, wherein the self-posting form is a Hypertext Markup Language (HTML) form that is configured to cause the client EHR application to transmit the resource to a GUI markup application executing on a second server computing device responsive to being loaded by the client EHR application, the GUI markup application is configured to generate GUI markups for multiple different EHR applications that each maintain respective patient health records, wherein the client computing device and the second server computing device are in communication over a second network connection;
- responsive to transmitting the indication to the server EHR application, receiving, from the server EHR application and over the network connection, the self-posting form;
- responsive to receiving the self-posting form from the server EHR application, transmitting the resource to the GUI markup application, wherein the GUI markup application generates a GUI markup based upon the resource;
- subsequent to transmitting the resource to the GUI markup application, receiving, from the GUI markup application and over the second network connection, the GUI markup; and
- responsive to receiving the GUI markup, rendering the GUI features on the display of the client computing device based upon the GUI markup, wherein the GUI features include the resource.

* * * * *